United States Patent [19]
Pagedas

[11] Patent Number: 5,895,393
[45] Date of Patent: Apr. 20, 1999

[54] SUTURE LOCK HOLDER

[76] Inventor: Anthony C. Pagedas, 8401 W. Edgerton, Greendale, Wis. 53129

[21] Appl. No.: 08/933,740

[22] Filed: Sep. 23, 1997

[51] Int. Cl.⁶ .................................................. A61B 17/24
[52] U.S. Cl. .................................................. 606/139
[58] Field of Search ........................... 606/139, 148, 606/151, 157, 158, 145, 146, 147, 205, 206, 207, 208, 222, 223, 225, 228, 232, 233; 24/16; 112/169, 80.03; 81/421, 418

[56] References Cited

U.S. PATENT DOCUMENTS

| | | | |
|---|---|---|---|
| 5,413,585 | 5/1995 | Pagedas | 606/232 |
| 5,417,701 | 5/1995 | Holmes | 606/148 |
| 5,522,820 | 6/1996 | Caspari et al. | 606/148 |
| 5,665,109 | 9/1997 | Yoon | 606/232 |
| 5,728,112 | 3/1998 | Yoon | 606/139 |
| 5,730,747 | 3/1998 | Ek et al. | 606/148 |

*Primary Examiner*—Michael Buiz
*Assistant Examiner*—Vikki Trinh
*Attorney, Agent, or Firm*—Ryan Kromholz & Manion, S.C.

[57] ABSTRACT

A self locking suture instrument having a body structure and an arm. The body structure comprises a first end, having a pair of forks and a body opening formed therein, and a second end. The arm has a first end and a second end, the second end being coupled to the main body structure, a top side and a bottom side. The arm has a releasable needle lock opening, being cone-shaped with a larger diameter on the top side of the arm and a corresponding smaller diameter on the bottom side of the arm. The arm has an open channel formed therein positioned on the top side of the arm and extending from the first end of the arm to the releasable needle lock opening. The arm has a recess formed therein, positioned on the top side of the arm and extending from the needle lock opening forward the second end of the arm.

10 Claims, 2 Drawing Sheets

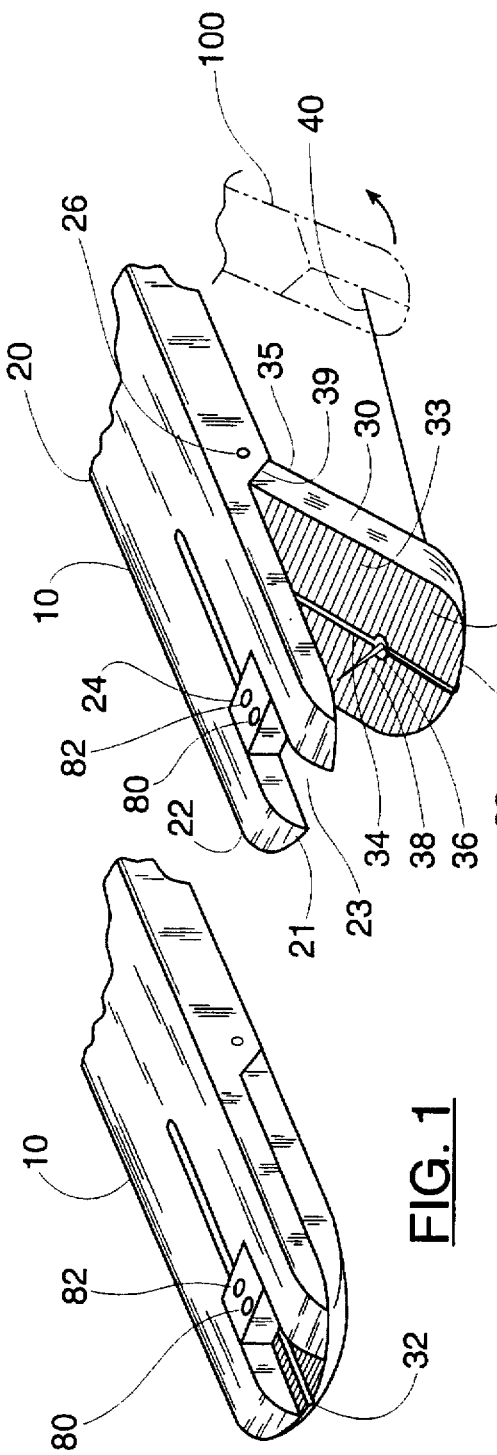
FIG. 1
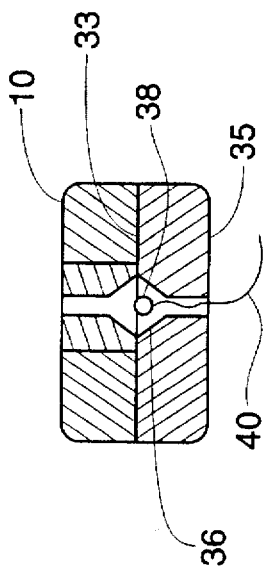
FIG. 4
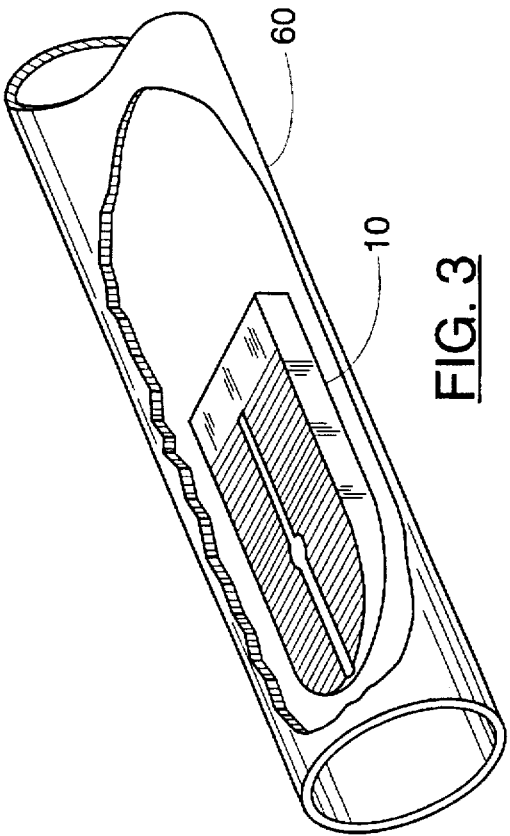
FIG. 2
FIG. 3

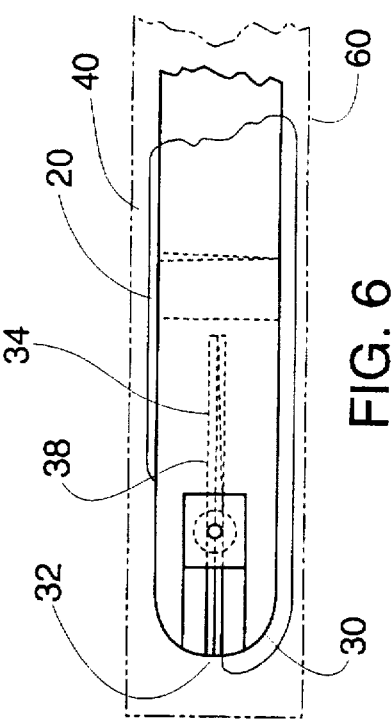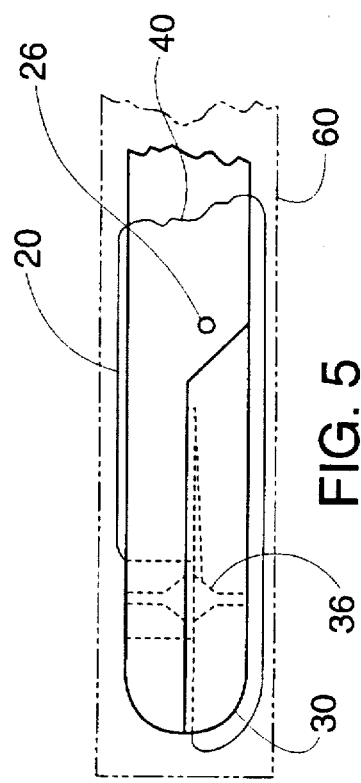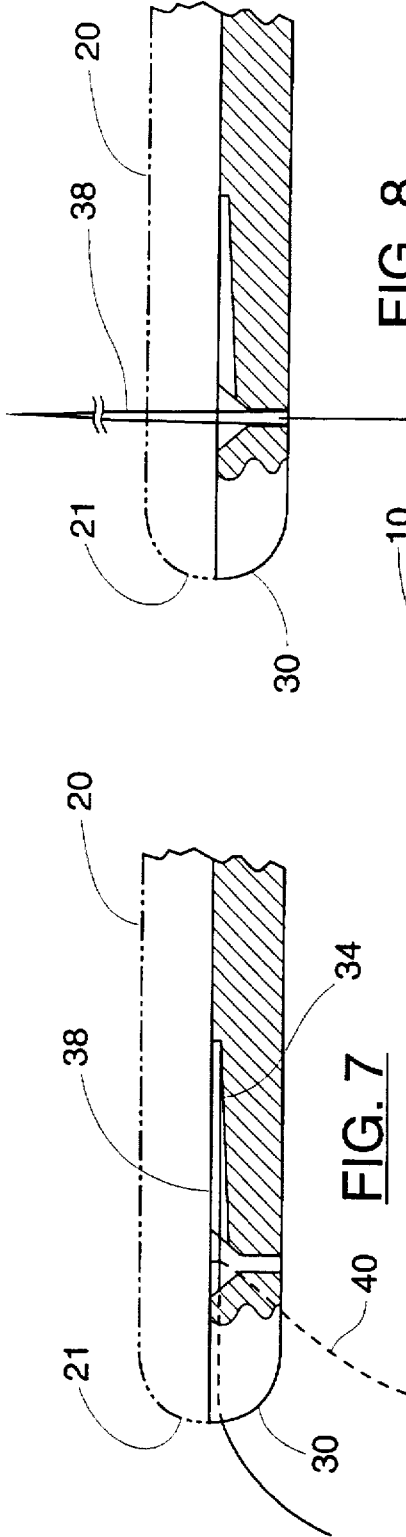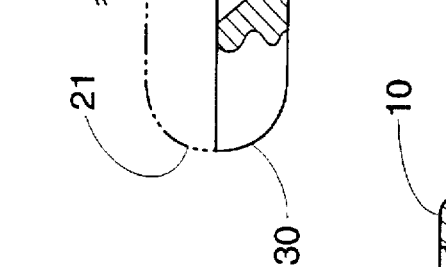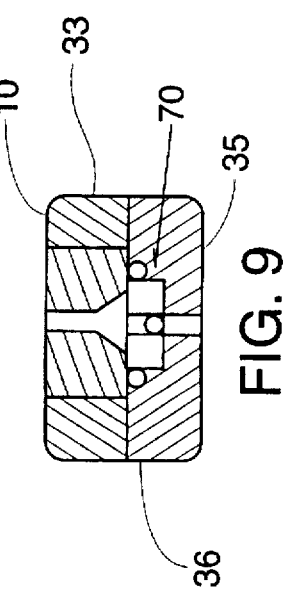

SUTURE LOCK HOLDER

BACKGROUND OF THE INVENTION

The need for this invention arises from surgical practice, particularly surgical practice using laparoscopic instruments involving small incisions, using a video camera lens or focusing device inserted in one of the incisions to view the field of the operation inside the patient and surgical instruments inserted in other incisions and manipulated from outside the patient's body using a TV screen or similar type of monitor for visualization, usually enlarged, to guide the work.

Anything that can reduce the number of steps to be performed in such an operation can markedly reduce the stress, both on the patient and on the doctor. Surgeons performing such operations are under considerable stress because remote manipulation using a monitor for visualization, rather than seeing the site of the operation directly requires the learning of a great many techniques that are radically different from those performed when the surgical site is open to view. These include indirect hand-eye coordination, and cooperation between surgeons to place and secure sutures.

The placing of sutures during a laparoscopic procedure typically requires two surgeons to cooperate in a multi-step process performed with multiple surgical instruments to manipulate the needle and suture and pass it back and forth from one to another, cooperation in tying the knot etc. This invention arose from the difficulty of such manipulations and the need to minimize that difficulty.

SUMMARY OF THE INVENTION

The present invention relies primarily on a body structure having connected thereto a pivotal arm. The body structure, which is located on the end of a modified laparoscopic surgical tool such as a clamp or cutting instrument, has a first end that terminates in a pair of forks defining a body opening that may be suitable for holding a self locking suture lock. The arm has a first end and a second end and also a top side and a bottom side, the arm being pivotally connected to the body at its second end. The top side of the arm is substantially flat, but may include ripples or other detent. The arm further has formed therein an open channel extending from the first end of the arm toward the second end of the arm to a releasable needle lock opening. The releasable needle lock opening is generally conical in shape, having a larger diameter on the top side of the arm and a smaller diameter on the bottom side of the arm. The open channel is in communication with the it conical interior of the releasable needle lock opening. Extending from the releasable needle lock opening toward the second end of the arm is a recess formed into the top side of the arm. The recess is capable of receiving a needle for suturing.

Prior to forming a suture, the suture needle is placed in the recess of the arm with the end of the suture needle connected to the suture thread closer to the releasable needle lock opening. It should be noted that the diameter of the needle lock opening on the bottom side of the arm has a slightly smaller diameter than that of the suture needle. However, the suture thread may freely pass through the open channel and through the needle lock opening. A self locking suture lock may be placed in the opening of the first end of the body. The self-locking suture lock itself comprises a body having a suture thread opening which may receive the suture material freely and which may then secure the suture material attached to the lock and a stitch lock opening designed to receive suture thread in only one direction and thereby to lock it against withdrawal. It is preferred that the structure of the body and the arm be arranged such that the needle lock opening of the arm aligns with the stitch lock opening of a self locking suture lock that can be mounted on the body. A suitable self locking suture lock is described in U.S. Pat. No. 5,413,585 and U.S. patent application Ser. No. 08/607,421; specifications of which are herein incorporated by reference.

A surgeon can laparoscopically form sutures at a surgical site by attaching suture thread to one end of the suture needle and positioning this suture needle inside a recess formed in said arm, the suture thread being passed through the open channel of the arm. The surgeon rotates the arm of the suturing instrument into a position adjacent to the body structure and introduces the suture instruments to the surgical site through a laparoscopic tube. The surgeon thereafter moves the arm away from the body structure thereby releasing the suture needle and applies a tension to the suture thread. The pull on the suture thread deflects the suture needle into the releasable needle lock opening. By once again rotating the arm into a position adjacent to the body of the suturing instrument the surgeon can pass the suture needle through the tissue to be sutured. If the surgeon so desires, a self locking suture lock can be placed in the opening at the end of the body prior to the introduction of the suturing instrument into the surgical site. To finish such a suture, the surgeon would pass the suture needle through the self locking suture lock. The suture needle would be then removed from the needle lock opening and tension would be applied to the suture thread in order to secure the suture. The suture lock would finally be removed from the body structure of the suture instrument, and the suture would be complete.

While the preferred embodiment described herein includes a substantially rigid body structure having an arm pivotally mounted thereto, an alternate embodiment comprises a first and a second arm hingedly coupled to each other and to a body structure at a hinge mechanism such that the first and second arms are mechanically separable from each other. The first arm, like the body structure of the preferred embodiment, may be arranged to include a suture lock mechanism. The second arm is similar to the arm of the preferred embodiment and includes a releasable needle lock opening having a generally conical shape with a large opening and a small opening such that said large opening is spatially oriented closest to the first arm. The second arm also has formed therein an open channel extending from the free end of the second arm towards the hinge mechanism and terminating at the releasable needle lock opening and a recess extending from the releasable needle lock opening towards the hinge mechanism. This alternate embodiment functions in the same manner as does the preferred embodiment.

The suture instrument eliminates a number of complex knot-tying steps and reduce the number of surgical laparoscopic tubes required to perform a particular surgery. This invention creates an easy sequence of surgical manipulations that reduces stress on the surgeon and the strain on the patient's body.

These and other benefits of the present invention will become apparent from the following detailed description taken in conjunction with the accompanying drawings.

DESCRIPTION OF THE DRAWINGS

FIG. 1 is a perspective view of the invention, showing the arm adjacent to the body structure and in the closed position.

FIG. 2 is a perspective view of the invention in the open position.

FIG. 3 is a fragmentary view showing the passage of the invention through a laparoscopic tube.

FIG. 4 is a cross-sectional view of the invention.

FIG. 5 is a side view of the invention in a laparoscopic tube.

FIG. 6 is a top view of the invention in a laparoscopic tube.

FIG. 7 is a cross-sectional view of the invention showing the suture needle laying in the recess.

FIG. 8 is a cross-sectional view of the invention showing the suture needle locked in the needle lock opening.

FIG. 9 is an end cross-sectional view of the present invention showing an alternative structure.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The preferred embodiment of the self locking suture instrument, designated generally as 10, is illustrated in FIGS. 1 and 2.

Referring to FIG. 2, the instrument that is the subject of the present invention 10 comprises a body structure 20 and an arm 30. The body 20 is rigid, having one end 21 comprising a pair of forks 22 forming an opening 23. The opening 23 may house a self locking suture lock 24. The arm 30 has a first end 37 and a second end 39. The arm's second end 39 is coupled to the body structure's midsection 20 through a pivot 26. The arm 30 comprises an open channel 32 and a recess 34 positioned on the arm's top side 33. The releasable needle lock opening 36 is cone-shaped, having a larger diameter on the top side 33 and a corresponding smaller diameter on the bottom side 35 of the arm 30. Since the diameter of the releasable needle lock 36 on the bottom side 35 is slightly smaller than the suture needle 38, the suture needle 38 is retained in the needle lock 36. The open channel 32 shown in FIG. 2 extends from the open end 37 of the arm 30 to the releasable needle lock opening 36. The recess 34 extends from the needle lock opening 36 toward the pivotally coupled end 39 of the arm 30. The top side 33 has ripples 31, substantially perpendicular on the open channel 32 and the recess 34.

Referring to FIG. 9, a cross-sectional view of an alternative embodiment is shown having a rectangular-shaped opening which replaces the cone-shaped opening. The purpose of this embodiment is to emphasize that a cone shaped opening need not be the only structural configuration for the needle lock opening 36.

As shown in FIGS. 2 and 5, it is contemplated that a self-locking suture lock 24 may be used with the suture instrument 10. Although the use of a suture lock as disclosed in U.S. Pat. No. 5,413,585 and U.S. patent application Ser. No. 08/607,421 is herein described, it should be noted that the present invention can be modified for use with other types of self-locking suture locks without departing from the spirit of the invention. The preferred type of self-locking suture lock 24 utilized with the present invention has a first suture thread opening 80 which may receive the suture material freely and which is also arranged to secure the suture material to the self-locking suture lock 24. The self-locking suture lock further has a stitch lock opening 82 designed to receive suture thread 40 in one direction only and thereby to lock it against withdrawal.

To facilitate the passage of the suture material 40 through the stitch-lock opening 82 of the self locking suture lock 24 the releasable needle lock opening 36 is generally aligned with the stitch lock opening 82. To place a stitch using the suturing instrument 10, the suture needle 38 is first positioned in the recess 34 with the end of the suture needle 38 connected to the suture thread 40 being closer to or adjacent the needle lock opening 36. The suture thread 40 may freely pass through the open channel 32 and the needle lock opening 36. Referring to FIGS. 1 and 3, the suture instrument 10, having the needle 38 positioned in the recess 34 and the pivotal arm 30 pivoted adjacent to the body structure 20, is inserted through the laparoscopic tube 60 to the site of the operation. The arm 30 is then moved away from the body structure 20, thereby releasing the suture needle 38. With the help of a tool 100, which may be pliers-like as shown in FIG. 2, a tension is applied to the suture thread 40. As shown in FIGS. 7 and 8 the pull applied to the thread 40 deflects the needle 38 into the needle lock opening 36. The cone-shaped opening 36 guides the needle 38 toward the smaller diameter of the needle lock 36 and substantially locks the needle 38 into place. The surgeon then brings the suture instrument 10 to the tissue to be sutured. The pivotal arm 30 is moved toward the body structure 20, passing the needle 38 through the tissue to be sutured and then through the stitch lock opening 82 of the self locking suture lock 24. The pliers-like tool 100 pulls the suture needle 38 through the self locking suture lock 24, thereby creating a tight stitch.

Once a stitch has been firmly placed at the surgical site, the suture instrument may be withdrawn. If one or more additional sutures are required at the surgical site, the surgeon has the choice of placing another self-locking suture lock 24 in the opening 23 of the body structure 20 of the suture instrument 10 or using a second, pre-loaded suture instrument 10. In either case, a suture instrument 10 having a self-locking suture lock 24 would be introduced to the surgical site. The surgeon may use the suture thread 40 and needle 38 already at the surgical site, or may introduce a new needle 38 and suture thread 40 to the surgical site. Again, in either case the needle 38 to be used is placed in the recess 34 and the attached suture thread The present invention allows a surgeon to easily and electively perform suturing in a laparoscopic operation. Needles or similar suturing devices of sizes heretofore considered to be to large for laparoscopic surgery may also be used thereby providing the surgeon with additional choices. Further, the ease of use provided by the present innovation greatly reduces the stress put on the surgeon during a laparoscopic procedure.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A self locking suture instrument to be used with surgical suture thread and a suture needle, said self locking suture instrument comprising:

a body structure having a first end and a second end;

said first end of said body structure having a body opening formed therein;

an arm, said arm having a first end and a second end, and having a top side and a bottom side;

said second end of said arm being coupled to said body structure;

said arm having a releasable needle lock opening;

said releasable needle lock opening being generally conical having a diameter on said top side of said arm larger than a diameter on said bottom side of said arm;

said arm having an open channel formed therein, said open channel extending from said first end of said arm to said releasable needle lock opening;

said arm having a recess formed therein, said recess positioned on said top side of said arm and extending from said releasable needle lock opening toward said second end of said arm.

2. The self locking suture instrument of claim 1, wherein said body opening of said first end of said body structure houses a self locking suture lock having a suture thread opening and a stitch lock opening.

3. The self locking suture instrument of claim 1 wherein said top side of said arm is a flat surface having ripples oriented at a substantially right angle with said open channel and said recess.

4. The self locking suture instrument of claim 1, wherein said needle lock opening on said bottom side of said arm has a slightly larger diameter than said suture needle.

5. The self locking suture instrument of claim 1, wherein said needle lock opening on said arm aligns with said stitch lock opening of said self locking suture lock.

6. The self locking suture instrument of claim 1, wherein said arm is pivotally coupled to said body structure's midsection.

7. A method for laparoscopic surgical suturing, using suture thread, a suture needle, and a self locking suture instrument having a body structure and an arm, comprising:

attaching suture thread to one end of a suture needle;

positioning said suture needle inside a recess formed in said arm;

rotating said arm to become adjacent to said body structure;

introducing said suture instrument through a laparoscopic tube;

moving said arm away from said body structure, thereby releasing said suture needle;

applying a tension to said suture thread, said tension thereby deflecting said suture needle into a releasable needle lock opening;

passing said suture needle through the tissue to be sutured.

8. The method recited in claim 7, having a first step comprising:

placing a self locking suture lock within said body structure of said self locking suture instrument.

9. The method recited in claim 7, having a final step comprising:

passing said suture needle through said self locking suture lock;

removing said suture needle from said needle lock opening;

removing said suture lock from said body structure of said self locking suture instrument.

10. A self-locking suture instrument to be used with surgical suture thread and a suture needle having a predetermined diameter, said self-locking suture instrument comprising:

a body structure having a first end and a second end;

said first end including a first arm and a second arm hingedly coupled to each other at a hinge mechanism and mechanically separable from each other;

said first arm including a suture lock mechanism;

said second arm including a releasable suture needle lock having a generally conical opening including a diameter spatially oriented closest to said suture lock larger than a diameter spatially oriented farthest from said suture lock;

said second arm having an open channel formed therein and extending from said generally conical opening; and said second arm having a recess formed therein, said recess extending a predetermined distance from said generally conical opening toward said hinge mechanism.

* * * * *